United States Patent
Bantia et al.

(10) Patent No.: US 6,656,915 B1
(45) Date of Patent: Dec. 2, 2003

(54) INHIBITING T-CELL PROLIFERATION

(75) Inventors: Shanta Bantia, Birmingham, AL (US); John A. Montgomery, Birmingham, AL (US); George A. Omura, Birmingham, AL (US)

(73) Assignee: Biocryst Pharmaceuticals, Inc., Birminghan, AL (US)

( * ) Notice: Subject to any disclaimer, the term of this patent is extended or adjusted under 35 U.S.C. 154(b) by 0 days.

(21) Appl. No.: 10/088,213

(22) PCT Filed: Sep. 15, 2000

(86) PCT No.: PCT/US00/25306
§ 371 (c)(1), (2), (4) Date: Jul. 30, 2002

(87) PCT Pub. No.: WO01/19375
PCT Pub. Date: Mar. 22, 2001

Related U.S. Application Data

(60) Provisional application No. 60/153,945, filed on Sep. 15, 1999.

(51) Int. Cl.[7] ............................................. A61K 31/505
(52) U.S. Cl. ...................... 514/43; 514/45; 514/259.31; 514/885; 514/922
(58) Field of Search ........................ 514/43, 45, 259.31, 514/885, 922

(56) References Cited

U.S. PATENT DOCUMENTS

| | | | |
|---|---|---|---|
| 4,985,433 A | * | 1/1991 | Secrist, III et al. ......... 514/258 |
| 4,988,702 A | | 1/1991 | Kostlan et al. |
| 5,985,848 A | | 11/1999 | Furneaux et al. |
| 6,228,847 B1 | | 5/2001 | Furneaux et al. |

OTHER PUBLICATIONS

"A promising drug for mesothelioma", Mikulski, S.M. et al., Phase II trial of a single weekly intravenous dose of ranpirnase in patients with unresectable malignant mesothelioma, J. Clin. Oncol. 20, pp. 274–281 (2002).

Purine nucleoside phosphorylase inhibitor BCX–1777 (Immucillin–H)—a novel potent and orally active immunosuppresive agent, Shanta Bantia, et al.; International Immunopharmacology 1 pp. 1199–1210 (2001).

"Immucillin H, a powerful transition–state analog inhibitor of purine nucleoside phosphorylase, seectively inhibits human T lympocytes" Greg A. Kicska, et al.; PNALS vol. 98, No. 8 pp. 4593–4598 (2001).

\* cited by examiner

*Primary Examiner*—Frederick Krass
(74) *Attorney, Agent, or Firm*—Connolly Bove Lodge & Hutz LLP

(57) ABSTRACT

Enhancement of T-cell proliferation in a host inhibition is provided by administering 2'-deoxyguanosine and/or prodrug thereof and a PNP inhibitor. The PNP inhibitor has a Ki value of 50 nanomoles or less.

9 Claims, No Drawings

INHIBITING T-CELL PROLIFERATION

CROSS-REFERENCE TO RELATED APPLICATION

This application is the U.S. national phase of International Application No. PCT/US00/25306 filed Sep. 15, 2000, which claims priority from U.S. Provisional Patent Application Ser. No. 60/153,945 filed Sep. 15, 1999.

TECHNICAL FIELD

The present invention relates to enhancing the inhibition of T-cell proliferation in a mammalian host and especially a human host. More particularly, the present invention is concerned with enhancing the inhibition of T-cell proliferation by administering 2'-deoxyguanosine and/or prodrugs thereof and certain PNP inhibitors which significantly prolong the half-life of the 2'-deoxyguanosine in a host. The PNP inhibitors employed according to the present invention possess Ki value of 50 nanomoles or less. The process of the present invention enhances the selective inhibition of T-cell proliferation without damaging humoral immunity, which renders the process potentially effective against disorders in which T-cells are pathogenic.

BACKGROUND OF INVENTION

Purine nucleoside phosphorylase (PNP) deficiency is a rare inherited disease accounting for approximately 4% of patients with severe combined immunodeficiency. In PNP deficiency, T- and B-cell immunity are affected. T-cell function may be profoundly deficient, may be normal at birth and then decrease with time, or may fluctuate repeatedly between low and normal. B-cell function can be normal but is deficient in approximately one third of patients. PNP protein is a trimer of approximately 90,000 daltons. It is found in most tissues of the body but is at highest levels in lymphoid tissues. This tissue distribution explains why the lymphoid system is predominantly affected in PNP deficiency. Many mechanisms have been proposed to explain the metabolic toxicity in PNP deficiency. The elevated dGTP found in PNP deficiency is thought to inhibit ribonucleotide reductase and, thus, impede cell division.

8-Aminoguanine given with 2'-deoxyguanosine inhibits the proliferation of human T-cells (CCRF-CEM and Molt-4 cells) in cultures. 8-Aminoguanosine, a soluble derivative which is converted in vivo to 8-aminoguanine, given to rats and dogs with 2'-deoxyguanosine causes a profound fall in peripheral blood lymphocytes and was shown in rats to produce increased levels of 2'-deoxyguanosine triphosphate (dGTP) in T-cells. To produce lymphopenia, inhibition of PNP was required, since 2'-deoxyguanosine alone did not significantly decrease cell counts.

9-(3-Pyridylmethyl)-9-deazaguanine, one of a family of PNP inhibitors, increases plasma inosine levels in humans, indicating effective inhibition of PNP, but it did not reduce T-cell counts. The cell culture and animal data presented above would indicate that in order to inhibit T-cell proliferation in humans, it would be necessary to provide exogenous 2'-deoxyguanosine, which would cause a sufficient accumulation of dGTP exclusively in the T-cells to inhibit their proliferation. However, exogenous 2'-deoxyguanosine rapidly degrades upon being administered to a host and therefore is not effective when administered alone.

SUMMARY OF INVENTION

It has been found according to the present invention that administering certain PNP inhibitors in addition to the exogenous 2'-deoxyguanosine and/or prodrug of 2'-deoxyguanosine results in significantly prolonging the half-life of the 2'-deoxyguanosine. Therefore, the combination of 2'-deoxyguanosine and/or prodrug of 2'-deoxyguanosine and the PNP inhibitors employed according to the present invention provides a potentially effective treatment against disorders in which activated T-cells are pathogenic. For instance, the implication of T-cells in the pathogenesis of various autoimmune diseases, including rheumatoid arthritis, systemic lupus erythematosus, psoriasis and type 1 diabetes strongly suggests that the present invention will be an effective therapy for these diseases. Other indications are the prevention of organ transplant rejection and the treatment of T-cell lymphomas and leukemias.

The PNP inhibitors employed according to the present invention have a Ki value of 50 nanomoles or less. The PNP inhibitor can be administered along with or prior to the 2'-deoxyguanosine and/or prodrug of 2'-deoxyguanosine.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

Best and Various Modes for Carrying Out Invention

The present invention relates to enhancing the inhibition of T-cell proliferation in a mammalian host in need of such treatment and especially a human host an effective amount of 2'-deoxyguanosine and/or prodrug of 2'-deoxyguanosine and an effective amount of at least one PNP inhibitor. The PNP inhibitor employed according to the present invention has a Ki value of 50 nanomoles or less.

Examples of suitable PNP inhibitors employed according to the present invention are those disclosed in U.S. Pat. Nos. 4,985,433; 4,985,434, 5,008,265; 5,008,270; 5,565,463 and 5,721,240 assigned to BioCryst Pharmaceuticals, Inc., disclosures of which are incorporated herein by reference. The preferred PNP inhibitor employed according to the present invention is 9-(3-pyridylmethyl)-9-deazaguanine.

Examples of suitable prodrugs of 2'-deoxyguanosine are represented by the following:

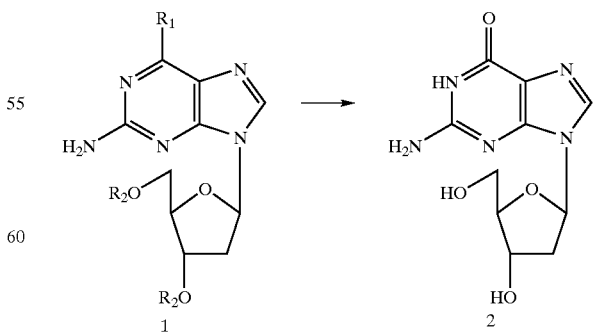

wherein $R_1$ is Cl, $NH_2$, $NHCH_3$, $R_3O$, $R_3S$, or H;

$R_2$ is acyl typically having 1 to 6 carbon atoms, and $R_3$ is alkyl typically having 1 to 3 carbon atoms and more typically 1 carbon atom.

The first five structural types (i.e.—$R_1$ is Cl, $NH_2$, $NHCH_3$, $R_3O$ or $R_3S$) are converted to 2'-deoxyguanosine in vivo by esterases and adenosine deaminase.

The sixth type ($R_1$=H) is oxidized in vivo to 2'-deoxyguanosine. Examples of these in vivo conversions are discussed in Montgomery, *Prog. in Med. Chem.* 7, 69 (1970) and Jones, *Antiviral Chemistry and Chemotherapy* 9, 283 (1998). Mixtures of prodrugs can be employed, if desired, as well as mixtures of one or more prodrugs with 2'-deoxyguanosine.

According to the process of the present invention, the PNP inhibitor is administered prior to or at the same time as the 2'-deoxyguanosine and/or prodrug of 2'-deoxyguanosine. The PNP should be present in the host's bloodstream with 2'-deoxyguanosine in order to effectively prolong the half-life of the 2'-deoxyguanosine to permit a sufficient accumulation of 2'-deoxyguanosine triphosphate in T-cells to prevent their proliferation. When the PNP inhibitor is administered prior to the 2'-deoxyguanosine and/or prodrug of 2'-deoxyguanosine it is typically administered up to about 1 hour prior to the 2'-deoxyguanosine and/or prodrug of 2'-deoxyguanosine.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mu of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A process for inhibiting T-cell proliferation in a mammalian host in need thereof by administering to said host an effective amount of at least one member selected from the group consisting of 2'-deoxyguanosine, prodrugs of 2'-deoxyguanosine and mixtures thereof, and at least one PNP inhibitor having a Ki of 50 nanomoles or less wherein said PNP inhibitor comprises 9-(3-pyridylmethyl)-9-deazaguanine.

2. The process of claim 1 wherein the PNP inhibitor is administered simultaneously with the at least one member or prior to the at least one member.

3. The process of claim 1 wherein the PNP inhibitor is administered up to about 1 hour prior to administering the at least one member.

4. The process of claim 1 which comprises orally administering the inhibitor.

5. The process of claim 4 which comprises administering the at least one member by infusion.

6. The process of claim 4 which comprises orally administering the at least one member.

7. The process of claim 1 wherein the at least one member is 2'-deoxyguanosine.

8. The process of claim 5 wherein the at least one member is 2'-deoxyguanosine.

9. The process of claim 6 wherein the at least one member is 2'-deoxyguanosine.

* * * * *